US011238373B2

(12) United States Patent
Misra et al.

(10) Patent No.: US 11,238,373 B2
(45) Date of Patent: Feb. 1, 2022

(54) DATA-DRIVEN AND INTELLIGENT CHARACTERIZATION OF SPATIAL DISTRIBUTIONS OF TRANSPORT PROPERTIES IN HETEROGENEOUS MATERIALS

(71) Applicant: The Board of Regents of the University of Oklahoma, Norman, OK (US)

(72) Inventors: Siddharth Misra, Norman, OK (US); Hao Li, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 231 days.

(21) Appl. No.: 16/529,462

(22) Filed: Aug. 1, 2019

(65) Prior Publication Data
US 2020/0041529 A1    Feb. 6, 2020

Related U.S. Application Data

(60) Provisional application No. 62/713,343, filed on Aug. 1, 2018.

(51) Int. Cl.
  *G06N 20/00* (2019.01)
  *G01N 15/08* (2006.01)
  *G01N 33/24* (2006.01)

(52) U.S. Cl.
  CPC ......... *G06N 20/00* (2019.01); *G01N 15/0826* (2013.01); *G01N 15/088* (2013.01); *G01N 33/24* (2013.01)

(58) Field of Classification Search
CPC .. G06N 20/00; G01N 15/0826; G01N 15/088; G01N 33/24
See application file for complete search history.

(56) References Cited

U.S. PATENT DOCUMENTS

| | | | |
|---|---|---|---|
| 2005/0010383 A1* | 1/2005 | Le Ravalec-Dupin | G01V 1/282 703/10 |
| 2013/0096898 A1* | 4/2013 | Usadi | G06F 30/23 703/10 |

(Continued)

OTHER PUBLICATIONS

Lillicrap, Timothy P., et al.; "Continuous Control with Deep Reinforcement Learning"; ICLR 2016; 14 pages.

(Continued)

*Primary Examiner* — Walter L Lindsay, Jr.
*Assistant Examiner* — Geoffrey T Evans
(74) *Attorney, Agent, or Firm* — Conley Rose, P. C.; Grant Rodolph; Jonathan K. Polk

(57) ABSTRACT

A method comprises obtaining temporal measurements associated with a heterogeneous material; building a numerical model of a material by assigning initial approximations to the temporal measurements; modifying the numerical model to create a modified numerical model; generating simulated temporal measurements associated with the temporal measurements using the modified numerical model; determining a reward, a penalty, or a modification based on a quality of a fit between the temporal measurements and the simulated temporal measurements; and updating the numerical model based on the reward, the penalty, or the modification.

26 Claims, 17 Drawing Sheets
(11 of 17 Drawing Sheet(s) Filed in Color)

(56) References Cited

U.S. PATENT DOCUMENTS

2018/0004865 A1* 1/2018 Borrel .................... E21B 41/00
2019/0162053 A1* 5/2019 Le Ravalec ............ G06F 30/20

OTHER PUBLICATIONS

Mnih, Volodymyr, et al.; "Human-Level Control through Deep Reinforcement Learning"; Nature; vol. 518; Feb. 26, 2015; Macmillan Publishers Limited; 13 pages.
Silver, David, et al.; "Mastering the Game of Go with Deep Neural Networks and Tree Search"; Nature; vol. 529 Jan. 28, 2016; Macmillan Publishers Limited; 20 pages.

* cited by examiner

800

| Reservoir Radius (ft) | Grid Size (ft²) | Initial Pressure (psi) | Formation Thickness (ft) | Porosity | Permeability 0 – 2000ft (md) | Permeability 2000 – 2800ft (md) | Permeability 2800–4040ft (md) |
|---|---|---|---|---|---|---|---|
| 4040 | 40 X 40 | 6000 | 10 | 0.25 | 100 | 100 | 100 |

| Well property | | Fluid property | |
|---|---|---|---|
| Well radius (ft) | Viscosity (cp) | Total Compressibility (psi$^{-1}$) | Flow Rate (bbl/day) |
| 0.25 | 0.4 | 0.000006 | 1 |

| Permeability 0-2,000 ft (md) | Permeability 2,000-2,800 ft (md) | Permeability 2,800-4,040 ft (md) |
|---|---|---|
| 5 | 10 | 1 |

1300

1700

ABSTRACT

DATA-DRIVEN AND INTELLIGENT CHARACTERIZATION OF SPATIAL DISTRIBUTIONS OF TRANSPORT PROPERTIES IN HETEROGENEOUS MATERIALS

CROSS-REFERENCE TO RELATED APPLICATIONS

This application claims priority to U.S. provisional patent application No. 62/713,343 filed on Aug. 1, 2018 by The Board of Regents of the University of Oklahoma and titled "Data-Driven Intelligent Characterization of Spatial Distributions of Transport Properties in Heterogeneous Media," which is incorporated by reference.

STATEMENT REGARDING FEDERALLY SPONSORED RESEARCH OR DEVELOPMENT

Not applicable.

BACKGROUND

Material analyses are important tools in many industries. Material analyses help determine types, characterizations, properties, and positions of those materials, as well as what substances and how much of those substances are in those materials. The properties include spatial features, internal arrangements, compositions, structures, distributions, and temporal changes. It is desirable to conduct material analyses in a cost-effective and operationally-convenient manner in the absence of the infrastructure needed to directly perform those material analyses. As a result, significant research is directed to reducing costs of material analyses, as well as improving materials analyses with an emphasis on reducing operational challenges.

BRIEF DESCRIPTION OF THE DRAWINGS

For a more complete understanding of this disclosure, reference is now made to the following brief description, taken in connection with the accompanying drawings and detailed description, wherein like reference numerals represent like parts. The patent or application file contains at least one drawing executed in color. Copies of this patent or patent application publication with color drawing(s) will be provided by the Office upon request and payment of the necessary fee.

FIG. 8 is a table of known reservoir properties and assumed permeability values of the three layers used for building the 2D numerical reservoir model on the designer platform prior to fitting the measurements and learning from the modifier, evaluator, and procedure learner modules.

FIG. 9 is a table of known well properties and formation fluid properties used for building the 2D numerical reservoir model on the designer platform prior to fitting the measurements and learning from the modifier, evaluator, and procedure learner modules.

DETAILED DESCRIPTION

Figure 1:
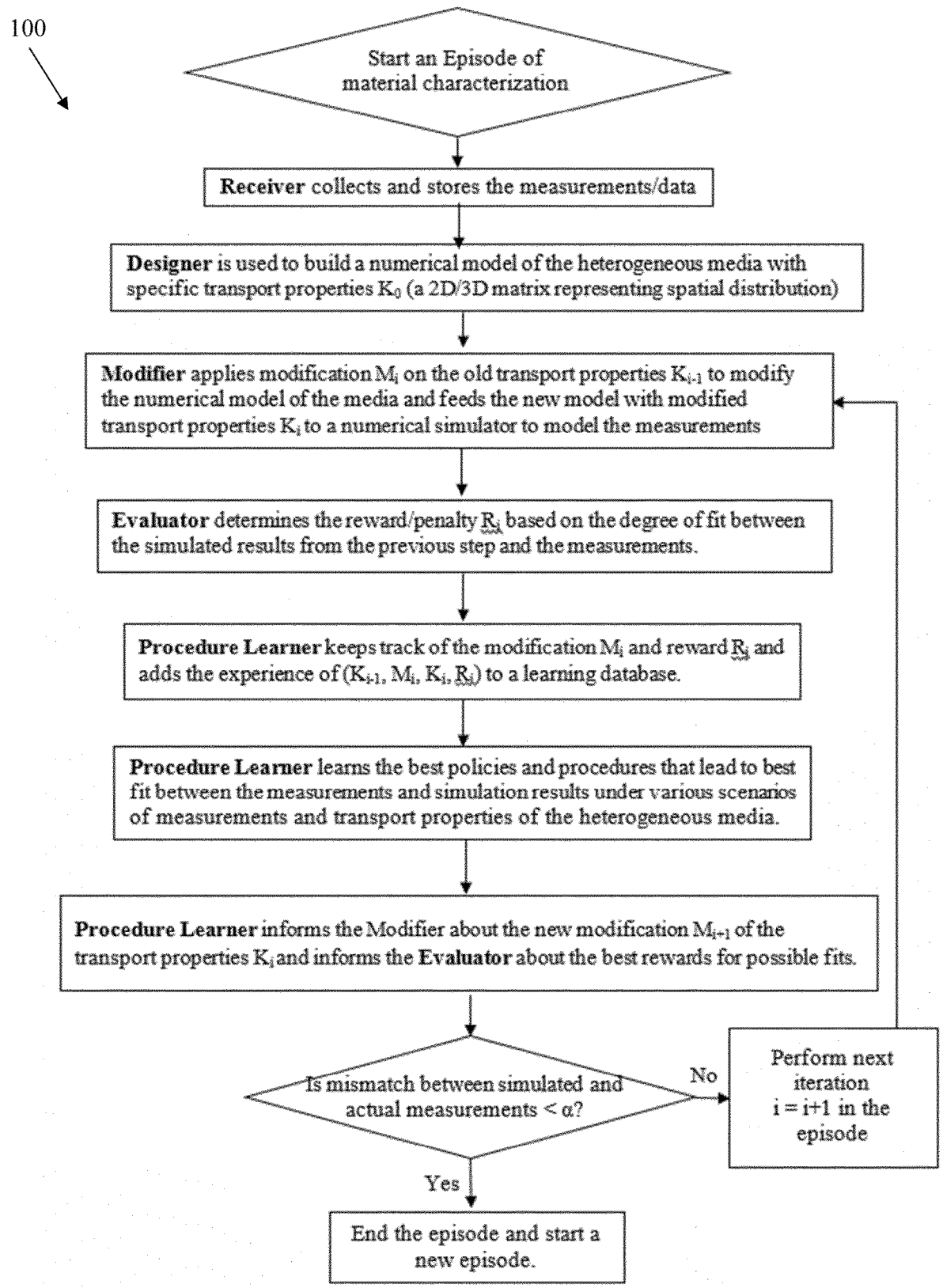
FIG. 1 is a flowchart illustrating a method of data-driven and intelligent characterization of spatial distributions of transport properties in heterogeneous materials according to an embodiment of the disclosure.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The following abbreviations apply:
ASIC: application-specific integrated circuit
bbl: barrel(s)
cP: centipoise(s)
CPU: central processing unit
DDPG: deep deterministic policy gradient
DSP: digital signal processor
EO: electrical-to-optical
FPGA: field-programmable gate array
ft: foot/feet
$ft^2$: square foot/feet
md: millidarc(y,ies)
OE: optical-to-electrical
psi: pound(s) per square inch
$psi^{-1}$: inverse psi
RAM: random-access memory
RF: radio frequency
RL: reinforcement learning
ROM: read-only memory
RX: receiver unit
SRAM: static RAM
TCAM: ternary content-addressable memory
TX: transmitter unit
1D: one-dimensional
2D: two-dimensional
3D: three-dimensional.

Before describing various embodiments of the present disclosure in more detail by way of exemplary description, examples, and results, it is to be understood as noted above that the present disclosure is not limited in application to the details of methods and apparatus as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and apparatus of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. A reference to degrees such as 1 to 90 is intended to explicitly include all degrees in the range.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error. Further, in this detailed description, each numerical value (e.g., temperature, time, mass, volume, concentration, etc.) should be read once as modified by the term "about" (unless already expressly so modified), and then read again as not so modified unless otherwise indicated in context. As noted above, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. Unless otherwise stated, the term "about" or "approximately", where used herein when referring to a measurable value such as an amount, length, thickness, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The spatiotemporal evolution of wave propagation and diffusive transport fronts in a heterogeneous medium/material depends on spatial distribution of location-specific transport properties, such as diffusivity, permeability, porosity, viscosity, compressibility, conductivity, and connectivity. Spatiotemporal evolution of wave propagation and diffusive transport fronts governs the location-specific temporal measurements related to the transport of energy, mass, and momentum such as current, heat flux, and flow rate, and the location-specific temporal measurements related to gradients that drive the transport processes such as pressure, voltage, potential, and chemical gradients. The disclosed embodiments process the temporal measurements related to the transport of energy, mass, and momentum, and the temporal measurements of gradients at one or more locations to perform intelligent characterization of the spatial distribution of transport properties of the heterogeneous material encountered during the spatiotemporal evolution of the wave propagation and diffusive transport fronts, which result in the temporal variations in the measurements. The intelligent characterization will lead to a high-resolution map of the spatial distribution of transport properties of the heterogeneous material encountered during the spatiotemporal evolution of the wave propagation and diffusive transport fronts.

Intelligent characterization refers to the ability of the disclosed system to learn and encode the sequence of modifications to the spatial distribution of transport properties based on the feedback from the forward simulator so as to obtain numerical predictions that are in good agreement with available temporal data. Intelligent characterization requires several automated and interdependent learning episodes, such that in each learning episode the disclosed system learns to reliably interact with the forward simulator to identify the sequence of modifications to the initial state of spatial distribution of transport properties under the constraints of available temporal data.

FIG. 1 is a flowchart illustrating a method 100 of data-driven and intelligent characterization of spatial distributions of transport properties in heterogeneous materials according to an embodiment of the disclosure. The following units/devices are implemented in the method 100: a receiver, a designer, a modifier, an evaluator, and a procedure learner.

From various locations in the heterogeneous material to be characterized, the receiver acquires, collects, compiles, and/or stores the temporal measurements related to the transport of energy, mass, and momentum and the temporal measurements related to the gradients that drive the transport processes such that these temporal measurements were acquired during the spatiotemporal evolution of wave propagation and diffusive transport fronts of energy, mass, and momentum in the heterogeneous material to be characterized.

The designer platform builds a numerical model of the spatial distribution of transport properties in the heterogeneous material by assigning the certain values of the various transport properties $K_0$ to various locations/grids of the numerical model. The designer platform performs this task with or without human input/assistance.

The modifier comprises various machine-learning/data-driven algorithms/methods/workflows and computation modules to modify the previously built/stored numerical model of the spatial distribution of transport properties in the heterogeneous material $K_{i-1}$. At the i-th learning iteration, the modifier applies a modification $M_i$ to an old spatial distribution of transport properties $K_{i-1}$ to obtain a new spatial distribution of transport properties $K_i$. Following that, the modifier feeds the new numerical model of the spatial distribution of transport properties in the heterogeneous material to a numerical simulator of wave propagation and/or diffusive transport fronts or to a full 3D multi-physics simulator for generating the simulated temporal measurements related to the transport of energy, mass, and momentum and the temporal measurements related to the gradients that drive the transport processes. In the proposed workflow, the modifier includes the simulator (forward modeling) module; however, both modules can be designed separately.

The evaluator comprises various machine-learning/data-driven algorithms/methods/workflows and computation modules to determine the reward/penalty $R_i$ based on the assessment of the quality of fit/match/agreement between the simulated and measured temporal measurements.

The procedure learner comprises various machine-learning/data-driven algorithms/methods/workflows and computation modules for four-fold applications: (1) keeping track of the modification $M_i$ determined by the modifier and the reward $R_i$ determined by the evaluator for any given misfit observed during the i-th learning iteration; (2) learning the best procedure from among the historical experiences comprising modifications, rewards, and corresponding misfits for the past iterations (0 to i−1) that leads to the best fit between the simulated and measured temporal measurements in a limited number of episodes under various scenarios of the initial values of the spatial distributions of transport properties in the heterogeneous material $K_0$; (3) informing the modifier about the modification $M_{i+1}$ of the current transport properties during the next iteration based on the current mismatch between the simulated and measured temporal data; and (4) informing the evaluator about the best reward $R_{i+1}$ based on the current mismatch and suggested modification $M_{i+1}$.

The proposed embodiment is not limited to the above-mentioned roles of the devices, namely a receiver, a designer, a modifier, an evaluator, and a procedure learner. The roles of devices can be combined, split, and modified to accomplish the desired task.

Unlike a supervised learning method, there is no labeling required from the user, and the user does not provide a training dataset for purposes of learning (i.e., data-driven modeling). Unlike an unsupervised learning method, clustering, transformation, feature extraction, and scaling of data may not take place during the learning process. The disclosed embodiments learn the proposed task by adopting RL techniques. Unlike the disclosed embodiments, RL implementations solve sequential decision problems using an agent to interact with an environment. The agent learns from the interaction history and improves its decision-making process. RL has been utilized in areas of game playing, where algorithms need to learn from various kinds of game states and a long-term strategy is needed for a good performance.

The disclosed system learns by undertaking several learning episodes. In each episode, the disclosed system matches the temporal measurements related to the transport of energy, mass, and momentum and the temporal measurements related to the gradients that drive the transport processes by learning to perform an optimal sequence of modifications to the spatial distribution of transport properties assigned to various spatial locations of the numerical model of the heterogeneous material at the start of an episode. The robustness of the sequence of modifications and rewards is learned after completing one episode of learning. Several such episodes are performed to identify the optimum procedure to learn the optimal sequence of modifications to fit the temporal measurements for purposes of intelligently characterizing the spatial distribution of transport properties in a heterogeneous material.

The disclosed system learns to interact with a numerical simulator of wave propagation and/or diffusive transport fronts of energy, mass, and momentum so as to generate simulated temporal measurements based on an optimum procedure that achieves the most desired fit between the simulated and measured temporal data. The evaluator determines a reward based on the match/fit. The optimum procedure is designed based on the best cumulative reward, including immediate reward and expected rewards for a limited number of future steps. The optimum procedure is a function of the quality of fit and the modifications along with the rewards based on the previous fits. An optimum procedure can be obtained by maximizing the cumulative reward in the least number of modifications. There can be other ways of identifying the optimum procedure that ensures the disclosed system learns to fit the measurements by optimally interacting with the forward simulator.

The embodiments improve the spatial characterization of transport properties of heterogeneous materials. Other approaches (such as data inversion and parameter estimation) do not use learning techniques to continuously learn from each of the several efforts to accurately model the measured data. Those other approaches use an optimization scheme coupled to the forward model to estimate the parameters of the forward model that generate simulated data that best fit the measured data. Furthermore, other approaches require human involvement that can be biased and inconsistent. Lower accuracy of human-assisted characterization technique is a challenge that can be addressed through the proposed system.

In contrast to those approaches, for each iteration in an episode and for each episode, the embodiments continuously learn from (1) the estimated model parameters (in this case, the spatial distribution of transport properties), (2) the misfit between the modeled and measured temporal measurements, and (3) the prior historical experiences (i.e., improvement/deterioration in match/fit) based on the modifications and resulting rewards. The concept of integrating the receiver, the designer, the modifier, the evaluator, and the procedure learner disrupts currently available technologies. This system identifies the optimum procedure for fitting the temporal measurements; consequently, learning the optimal sequence of modifications to the initial assumption of spatial distribution of transport properties for accurately characterizing the heterogeneous material under constraints of the available data and the available physics-based numerical simulator of the process of interest. Importantly, the system continuously improves with greater exposure to data, measurements, cases, learning episodes, and characterization tasks. The embodiments improve the accuracy of characterization by removing human involvement and implementing an automated learning-based system to identify the optimum procedure for characterizing heterogeneous materials.

Figure 2A:
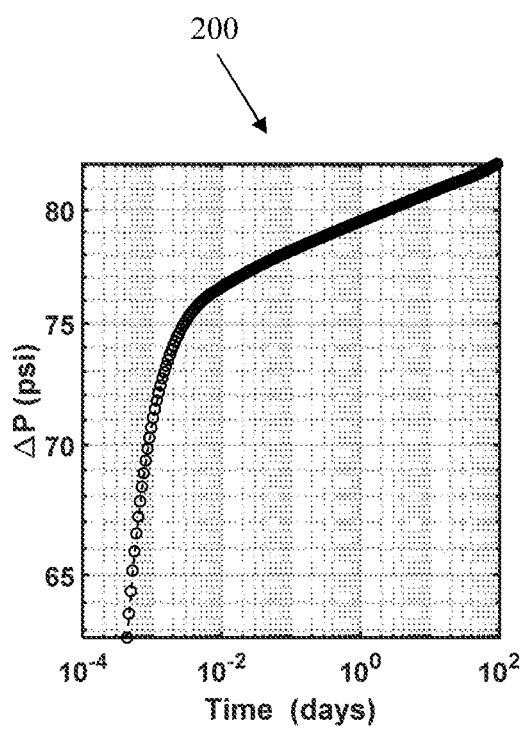
FIG. 2A is a graph showing pressure changes measured for a vertical well producing in a heterogeneous, hydrocarbon-bearing, ideal, cylindrical reservoir of known thickness buried thousands of feet below the ground. The top view of the ideal cylindrical reservoir model is made of three concentric layers as shown in FIG. 6A.
Figure 2B:
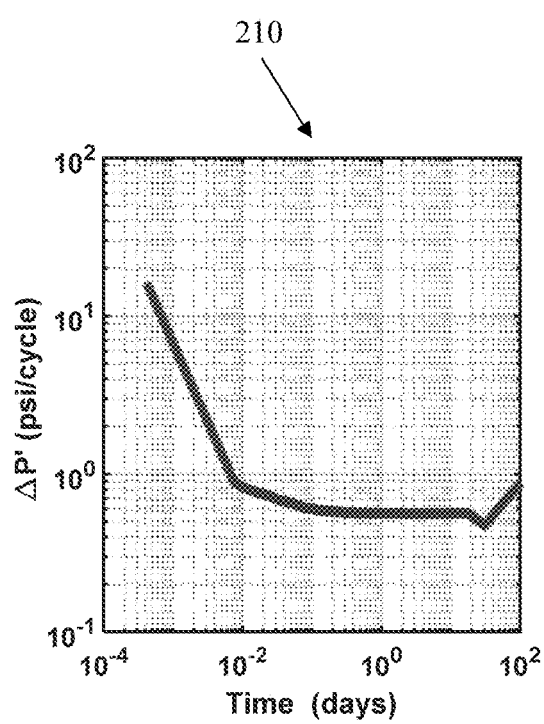
FIG. 2B is a graph showing Bourdet-type pressure derivative responses measured for a vertical well producing in a heterogeneous, hydrocarbon-bearing, ideal, cylindrical reservoir of known thickness buried thousands of feet below the ground. The top view of the ideal cylindrical reservoir model is made of three concentric layers as shown in FIG. 6A.
Figures 6A, 6B:
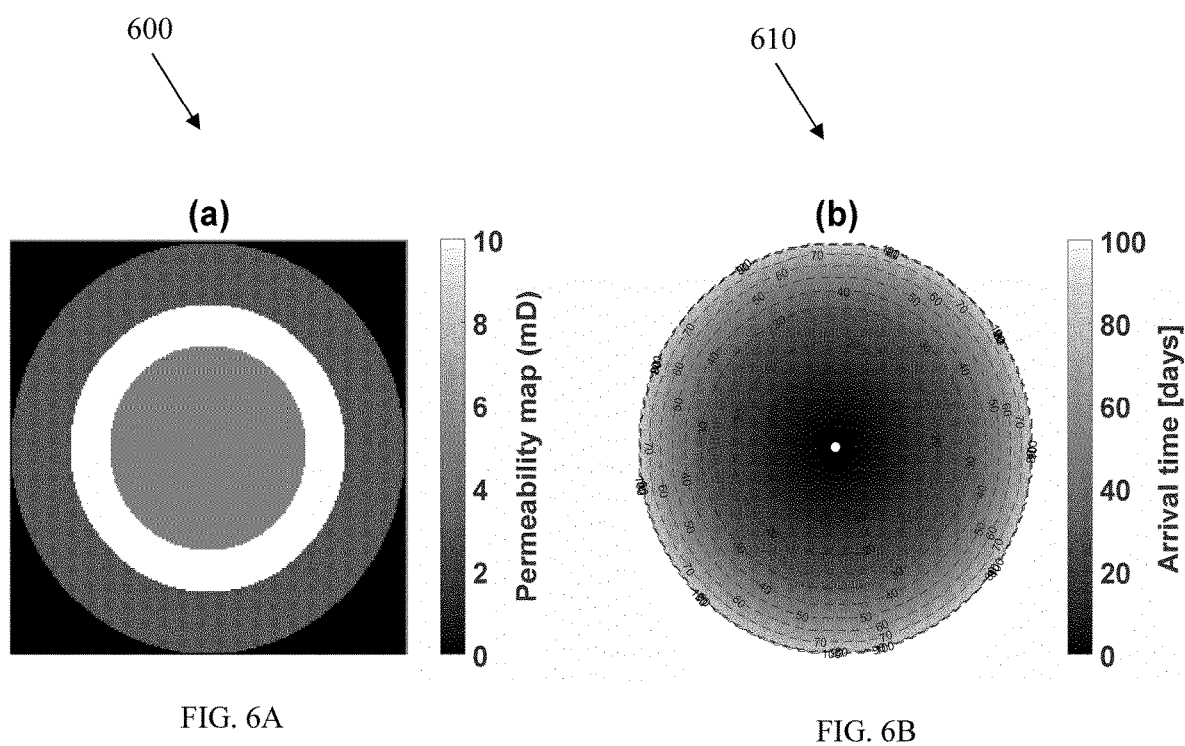
FIG. 6A is a permeability (transport property of reservoir model) distribution in the 2D reservoir model generated using the embodiments by processing the pressure transient measurements shown in FIGS. 2A and 2B. In these embodiments, permeability of the reservoir is characterized by processing the pressure transient responses measured in a vertical well.
FIG. 6B shows the propagation of a pressure front in terms of travel times in the 2D reservoir model.

FIG. 2A is a graph 200 showing pressure change measured for a vertical well producing in a heterogeneous, hydrocarbon-bearing, ideal, cylindrical reservoir of known thickness buried thousands of feet below the ground. The top view of the ideal cylindrical reservoir model is made of three concentric layers as shown in FIG. 6A. FIG. 2B is a graph 210 showing Bourdet-type pressure derivative responses measured for a vertical well producing in a heterogeneous, hydrocarbon-bearing, ideal, cylindrical reservoir of known thickness buried thousands of feet below the ground. The top view of the ideal cylindrical reservoir model is made of three concentric layers as shown in FIG. 6A. In one implementation, the receiver collects pressure transient responses comprising pressure change and pressure derivatives (FIGS.

2A and 2B) along with the flow rate, of a vertical well producing in a heterogeneous, hydrocarbon-bearing, ideal, cylindrical reservoir of known thickness buried thousands of feet below the ground. The intelligent characterization involves the estimation of spatial distribution of permeability (one specific transport property, assuming other transport properties to be constant) in the entire heterogeneous, hydrocarbon-bearing, ideal cylindrical reservoir (material). The reservoir has similar properties in the vertical direction; consequently, the entire ideal cylindrical reservoir can be represented as a 2D circular region (similar to FIG. 6A).

The designer builds the 2D/3D numerical model of the heterogeneous reservoir and assigns initial values of transport properties (e.g., permeability) $K_0$ to the numerical model assuming certain or no transport properties to be constant valued over the entire numerical model of the heterogeneous reservoir.

FIG. 8 is a table 800 of known reservoir properties and assumed permeability values of the three layers used for building the 2D numerical reservoir model built on the designer platform prior to fitting the measurements and learning from the modifier, evaluator, and procedure learner modules. FIG. 9 is a table 900 of known well properties and formation fluid properties used for building the 2D numerical reservoir model on the designer platform prior to fitting the measurements and learning from the modifier, evaluator, and procedure learning modules. The properties assumed for building the numerical reservoir model on the designer platform are listed in FIGS. 8-9. The resulting numerical reservoir model depicts an ideal cylindrical reservoir of uniform thickness with three concentric layers, which are assumed to have similar permeability (similar to FIG. 6A).

Permeability values in the entire numerical model of the reservoir are assigned to be 100 and before starting each episode of the learning process aimed towards characterizing the spatial distribution of permeability in the heterogeneous reservoir. The modifier modifies the 2D numerical model of the hydrocarbon-bearing reservoir by applying the modification $M_i$ to older permeability distribution $K_0$ by assigning new values to each location in the reservoir model. The modifier feeds the modified 2D numerical model to a fast-marching reservoir simulator (the choice of simulator depends on the temporal measurements and the underlying physical phenomena). For purposes of demonstration in this embodiment, the modification $M_i$ applied to the reservoir permeability values at different locations in the reservoir model is a continuous scalar multiplier (can be continuous or discrete) in the range of 0.5 to 2. At the i-th learning iteration, the modified 2D reservoir model with the modified reservoir permeability values $K_i$ is fed to the fast-marching reservoir simulator.

The simulator generates the modeled responses that should match the measured pressure transient responses, comprising pressure change and pressure derivatives (FIGS. 2A and 2B), of a vertical well producing in a heterogeneous, hydrocarbon-bearing, ideal, cylindrical reservoir of uniform thickness buried thousands of feet below the ground. The evaluator assesses the quality of fit between the modeled and measured pressure transient responses and determines a reward $R_i$ based on the quality of the fit. The learning experience for the i-th iteration involves the following sequence: $K_{i-1}$, $M_i$, $K_i$, and $R_i$ which is recorded as an experience by the procedure learner in a training database.

In the next iteration (i+1), reservoir permeability values $K_i$ at different locations of the 2D reservoir model are modified by the modifier for a better match between modeled and measured pressure transient responses. The procedure learner uses the historical experiences stored in the training database to guide the modifier to apply the modification $M_{i+1}$ and the evaluator to give the right reward $R_{i+1}$ in the next iteration (i+1). The procedure learner learns the best procedure to modify the reservoir permeability values at various locations of the heterogeneous reservoir model under various reservoir scenarios of varying permeability distributions and various pressure transient response measurements.

Such iterations are performed for a specific number of times or until the quality of fit is above a certain threshold; one set of iterations is referred to as one learning episode. Several learning episodes are performed to identify the optimum procedure that ensures that the proposed method and system learn to efficiently and effectively perform an intelligent characterization and generate the map of permeability distribution of the heterogeneous reservoir.

Figure 3:
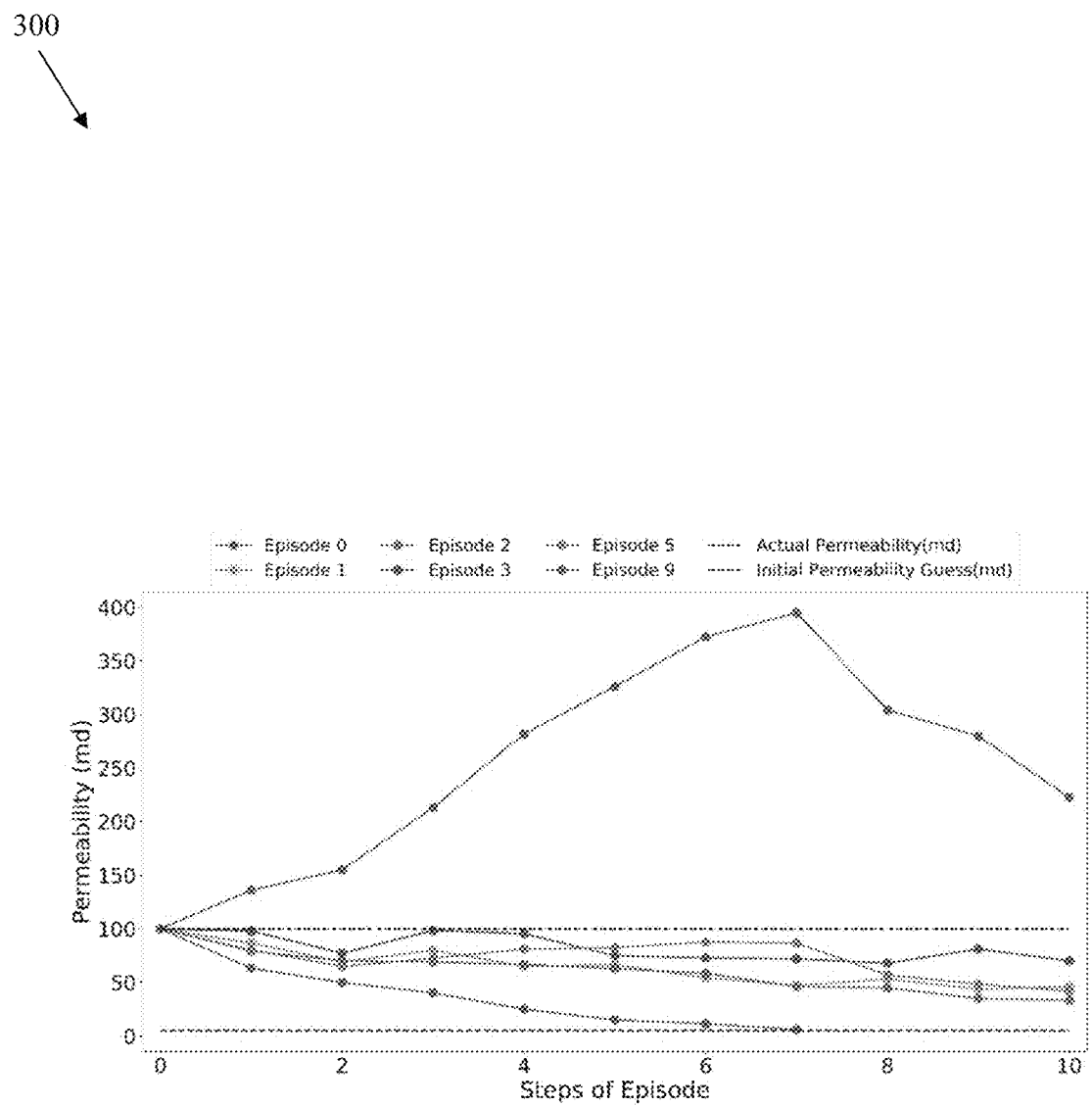
FIG. 3 is a graph showing the intelligent data-driven characterization of the innermost concentric layer in the reservoir model as a 5 md layer, similar to that shown in FIG. 6A, when initialized as a 100 md zone.
Figure 4:
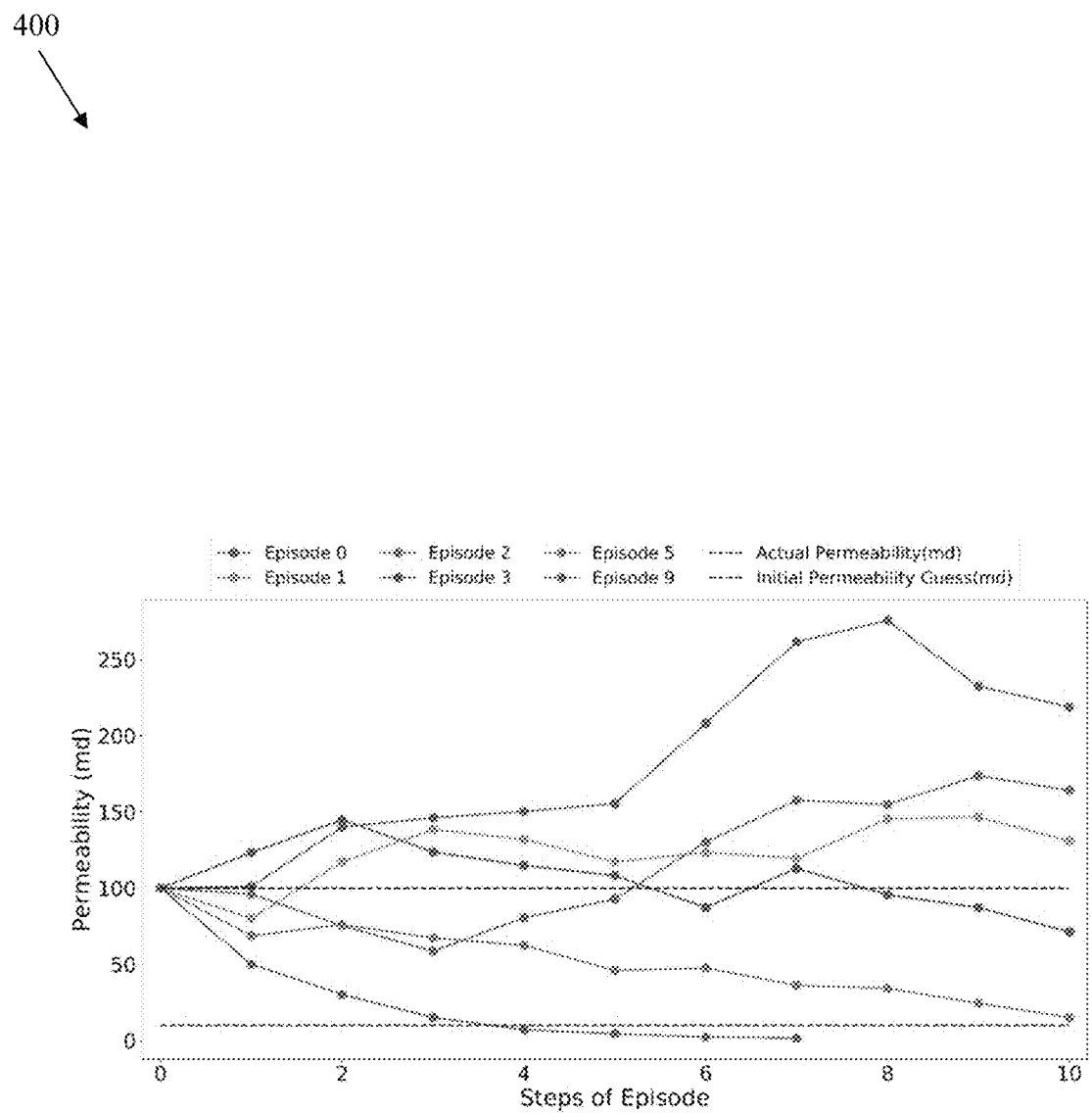
FIG. 4 is a graph showing the intelligent data-driven characterization of the middle concentric layer in the reservoir model as a 10 md layer, similar to that shown in FIG. 6A, when initialized as a 100 md zone.
Figure 5:
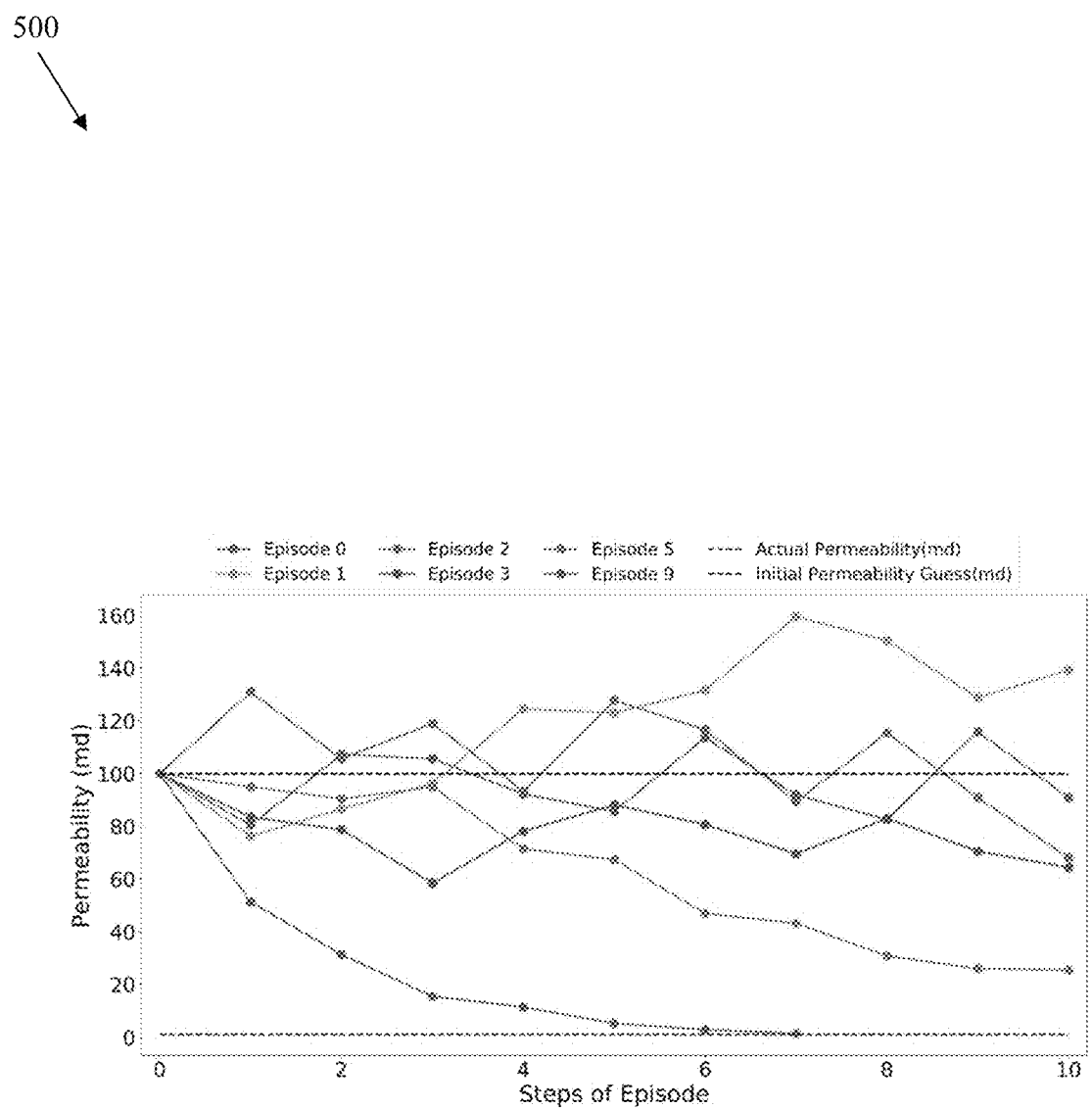
FIG. 5 is a graph showing the intelligent data-driven characterization of the outermost concentric layer in the reservoir model as a 2 md layer, similar to that shown in FIG. 6A, when initialized as a 100 md zone.

FIG. 3 is a graph 300 showing the intelligent data-driven characterization of the innermost concentric layer in the reservoir model as a 5 md layer, similar to that shown in FIG. 6A, when initialized as a 100 md zone. FIG. 4 is a graph 400 showing the intelligent data-driven characterization of the middle concentric layer in the reservoir model as a 10 md layer, similar to that shown in FIG. 6A, when initialized as a 100 md zone. FIG. 5 is a graph 500 showing the intelligent data-driven characterization of the outermost concentric layer in the reservoir model as a 2 md layer, similar to that shown in FIG. 6A, when initialized as a 100 md zone. The data-driven intelligent characterization of the three concentric layers is achieved by processing the transient responses shown in FIGS. 2A and 2B using the proposed method and system outlined in FIG. 1. The innermost, middle, and outermost layers are characterized as layers with permeabilities of 5, 10, and 1 md, respectively. For the purposes of the proposed characterization, the three concentric layers in the 2D reservoir model are initialized as layers with permeability of 100 md. FIGS. 8 and 9 list the properties assumed or known for the desired characterization. The three layers are characterized simultaneously by implementing the workflow shown in FIG. 1. For the three layers, with the increase in learning episodes, the rate and accuracy of characterization of the three concentric reservoir layers improves, as shown in FIGS. 3, 4, and 5. This indicates the intelligent characterization achieved by the embodiments.

In this implementation, the reservoir model was built on the designer platform with a uniform constant permeability of 100 md across the entire reservoir with a reservoir boundary located at a distance of 4,040 ft from the center of the well. FIG. 8 is a table of known reservoir properties and assumed permeability values of the three layers used for building the 2D numerical reservoir model on the designer platform prior to fitting the measurements and learning from the modifier, evaluator, and procedure learner modules. FIG. 9 is a table of known well properties and formation fluid properties used for building the 2D numerical reservoir model on the designer platform prior to fitting the measurements and learning from the modifier, evaluator, and procedure learner modules.

FIG. 6A is a permeability (transport property of reservoir model) distribution 600 in the 2D reservoir model generated using the embodiments by processing the pressure transient measurements shown in FIG. 2. FIG. 6B shows the propagation of a pressure front 610 in terms of travel times in the 2D reservoir model. The innermost, middle, and outermost zones have permeabilities of 5 md, 10 md, and 1 md, respectively, as generated using the embodiments.

Figure 7:
FIG. 7 shows a schematic of iterative steps for determining the optimum procedure for performing data-driven and intelligent characterization of heterogeneous materials.
Figure 7:
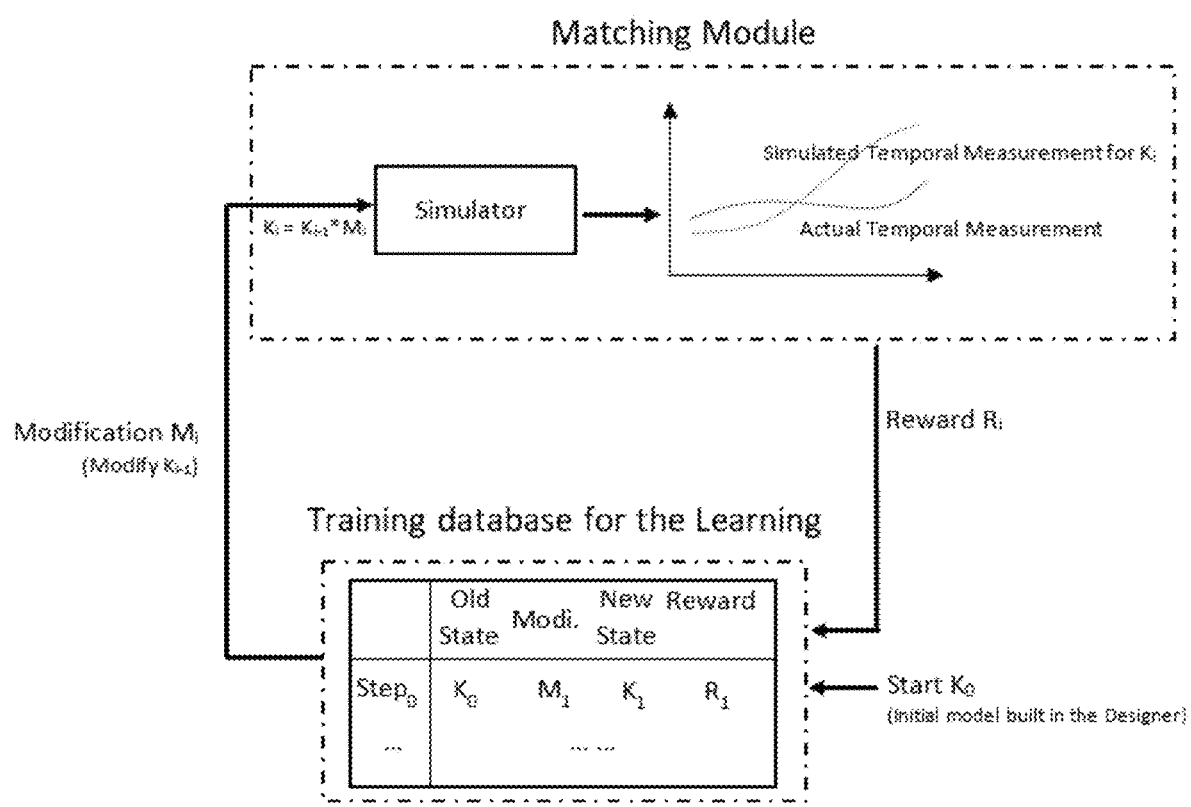

FIG. 7 shows a schematic of iterative steps for determining the optimum procedure for performing data-driven and intelligent characterization of heterogeneous materials. FIG. 7 is an alternate representation of FIG. 1.

Figure 10:
FIG. 10 is a table of reservoir permeability distribution of the reservoir, also shown in FIG. 6A, generated using the embodiments by processing the pressure transient measurements, shown in FIGS. 2A and 2B, using the proposed data-driven intelligent characterization system, described in FIG. 1 and FIG. 7.

FIG. 10 is a table 1000 of reservoir permeability distribution of the reservoir, also shown in FIG. 6A, generated using the embodiments by processing the pressure transient measurements, shown in FIGS. 2A and 2B, using the proposed data-driven characterization system, described in FIG. 1 and FIG. 7.

Figure 11:
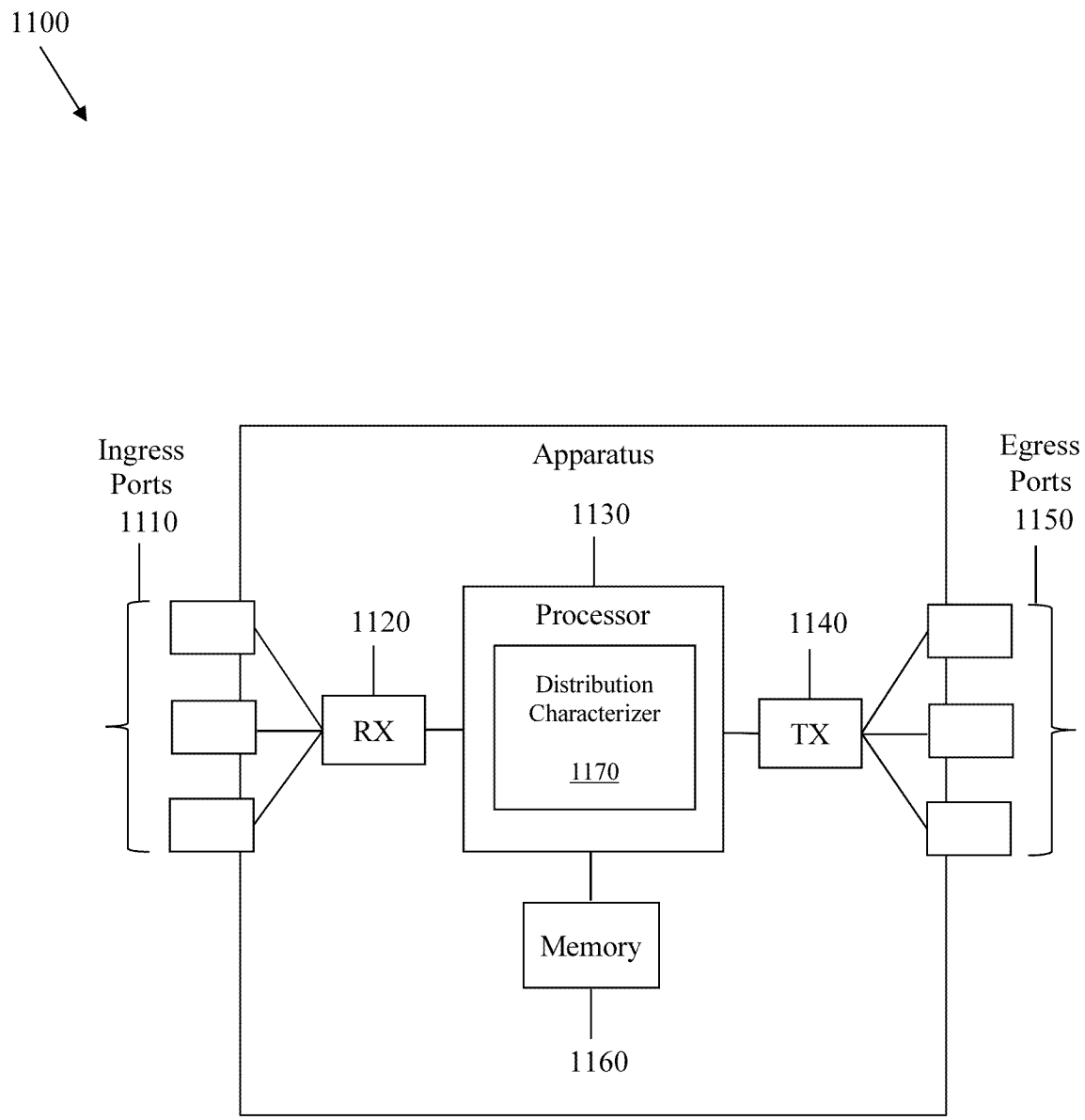
FIG. 11 is a schematic diagram of an apparatus according to an embodiment of the disclosure.

FIG. 11 is a schematic diagram of an apparatus 1100 according to an embodiment of the disclosure. The apparatus 1100 may implement the disclosed embodiments. The apparatus 1100 comprises ingress ports 1110 and an RX 1120 for receiving data; a processor, logic unit, baseband unit, or CPU 1130 to process the data; a TX 1140 and egress ports 1150 for transmitting the data; and a memory 1160 for storing the data. The apparatus 1100 may also comprise OE components, EO components, or RF components coupled to the ingress ports 1110, the RX 1120, the TX 1140, and the egress ports 1150 for ingress or egress of optical, electrical signals, or RF signals.

The processor 1130 is any combination of hardware, middleware, firmware, or software. The processor 1130 comprises any combination of one or more CPU chips, cores, FPGAs, ASICs, or DSPs. The processor 1130 communicates with the ingress ports 1110, the RX 1120, the TX 1140, the egress ports 1150, and the memory 1160. The processor 1130 comprises a distribution characterizer 1170, which implements the disclosed embodiments. The inclusion of the distribution characterizer 1170 therefore provides a substantial improvement to the functionality of the apparatus 1100 and effects a transformation of the apparatus 1100 to a different state. Alternatively, the memory 1160 stores the distribution characterizer 1170 as instructions, and the processor 1130 executes those instructions.

The memory 1160 comprises any combination of disks, tape drives, or solid-state drives. The apparatus 1100 may use the memory 1160 as an over-flow data storage device to store programs when the apparatus 1100 selects those programs for execution and to store instructions and data that the apparatus 1100 reads during execution of those programs. The memory 1160 may be volatile or non-volatile and may be any combination of ROM, RAM, TCAM, or SRAM.

Demonstration of applicability was shown on reservoir models with three concentric layers of varied permeability. Nonetheless, the proposed workflow of data-driven intelligent characterization can be applied to the characterization of any heterogeneous or homogenous material of any shape and size in subsurface, surface, air, or space environments. The proposed embodiments employ a numerical model of the material with or without an initial approximation of 1D, 2D or 3D spatial distributions of one or many transport properties of the material. Then the embodiments process the temporal measurements related to the transport of energy, mass, and momentum such as current and flow rate, and the temporal measurements related to gradients that drive the transport processes such as pressure, voltage, potential, and chemical gradients.

Figure 12:
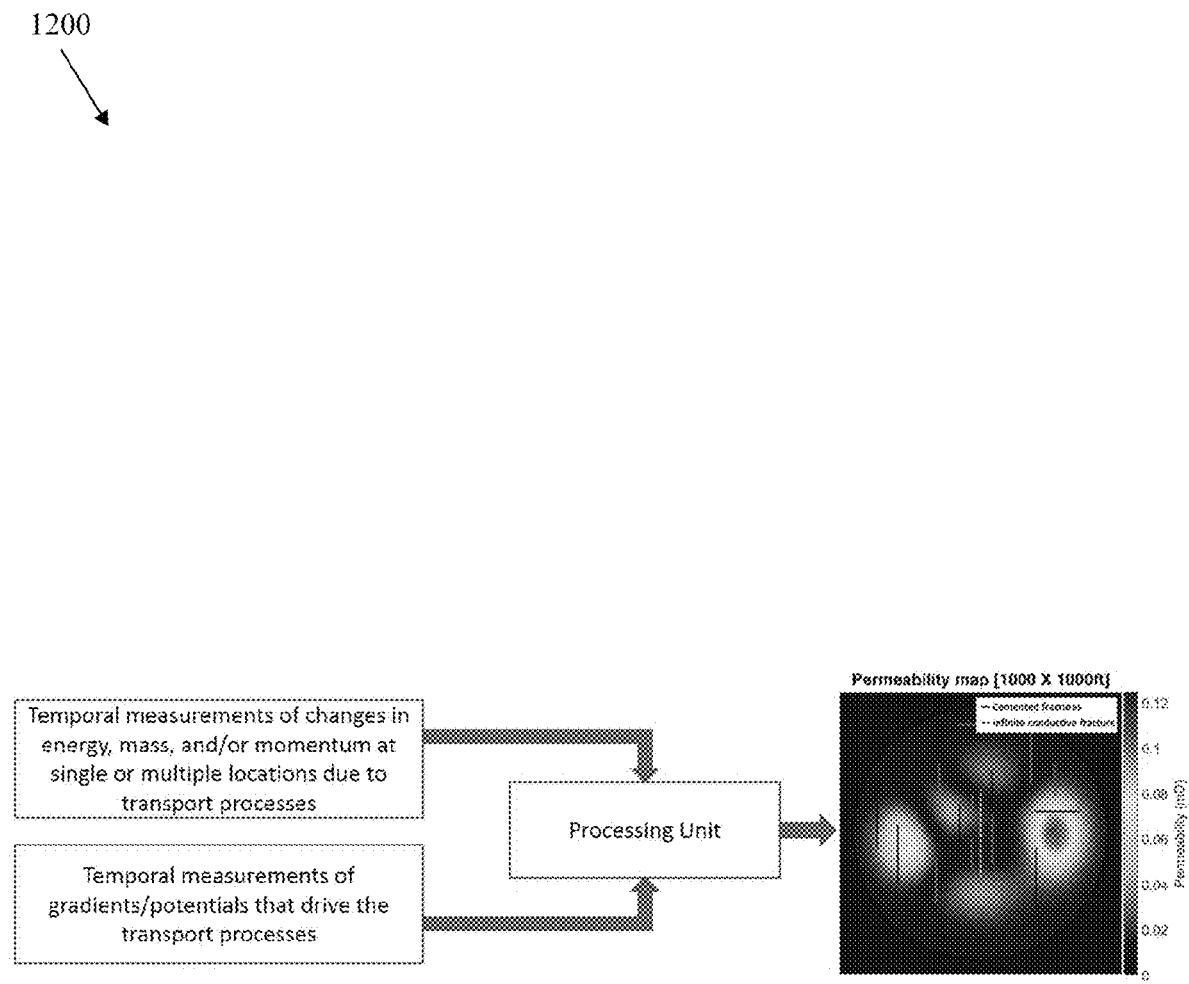
FIG. 12 is a schematic diagram showing that a processing unit captures the first temporal measurements associated with transport of energy, mass, or momentum and second temporal measurements associated with gradients resulting from the transport mechanisms.

The embodiment comprising receiver, designer, modifier, evaluator, and procedure learner can be applied to another example involving the characterization/mapping of spatial distribution of permeability of a heterogeneous ideal cylindrical reservoir by processing the temporal measurements of pressure change, Bourdet-type derivative of pressure change, and flow rate (FIG. 12).

FIG. 12 is a schematic diagram 1200 showing that a processing unit captures the first temporal measurements associated with transport of energy, mass, or momentum and second temporal measurements associated with gradients resulting from the transport mechanisms. The goal of the processing unit is to spatially characterize the heterogeneous material that generated the first and second temporal measurements.

Figure 13:
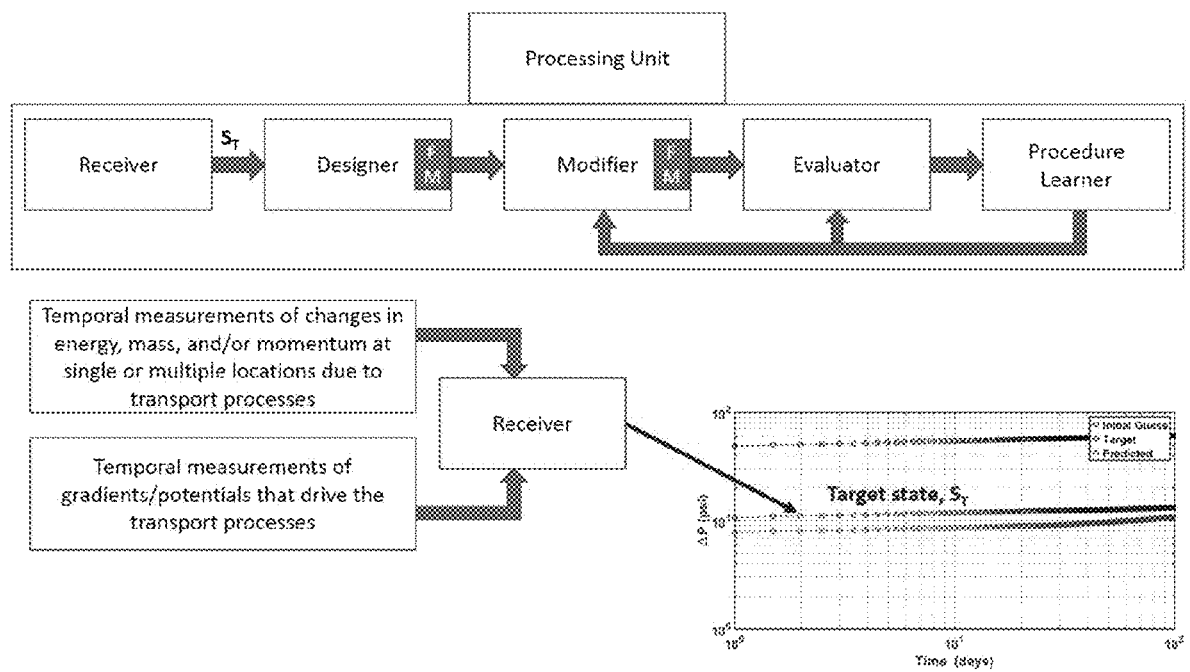
FIG. 13 is a schematic diagram showing that the receiver acquires, collects, compiles, and/or stores the temporal measurements related to the transport of energy, mass, and momentum and the temporal measurements related to the gradients that drive transport processes.

FIG. 13 is a schematic diagram 1300 showing that the receiver acquires, collects, compiles, and/or stores the temporal measurements related to the transport of energy, mass, and momentum and the temporal measurements related to the gradients that drive transport processes. The temporal measurements were acquired during the spatiotemporal evolution of wave propagation and diffusive transport fronts of energy, mass, and momentum in the heterogeneous material to be characterized. Temporal measurements in this example include pressure change, flow rate, and Bourdet-type pressure derivative responses of a vertical well in a heterogeneous ideal cylindrical reservoir. Temporal measurements are collectively referred as the target state denoted by $S_T$.

Figure 14:
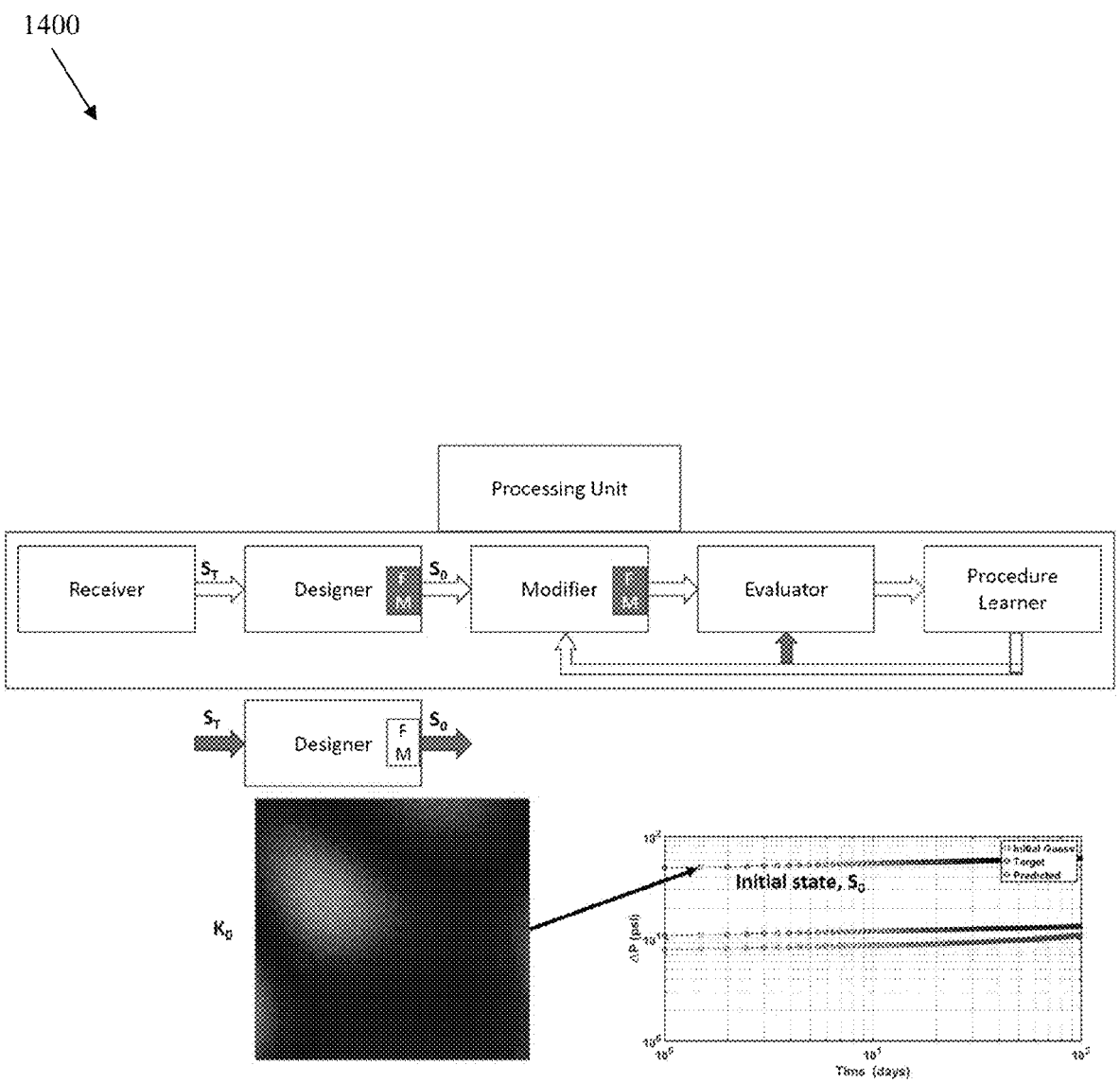
FIG. 14 is a schematic diagram showing that the designer platform builds a numerical model of the spatial distribution of transport properties in the heterogeneous material by assigning the initial values of the various transport properties $K_0$ to various locations/grids of the model.

FIG. 14 is a schematic diagram 1400 showing that the designer platform builds a numerical model of the spatial distribution of transport properties in the heterogeneous material by assigning the initial values of the various transport properties $K_0$ to various locations/grids of the model. Initial spatial distribution $K_0$ built by the designer when fed to the simulator/forward-model (denoted by FM) generates an initial state denoted by $S_0$. Generally, $S_T$ should guide initialization of $K_0$ so that $S_T$ and $S_0$ are not very different.

Figure 15:
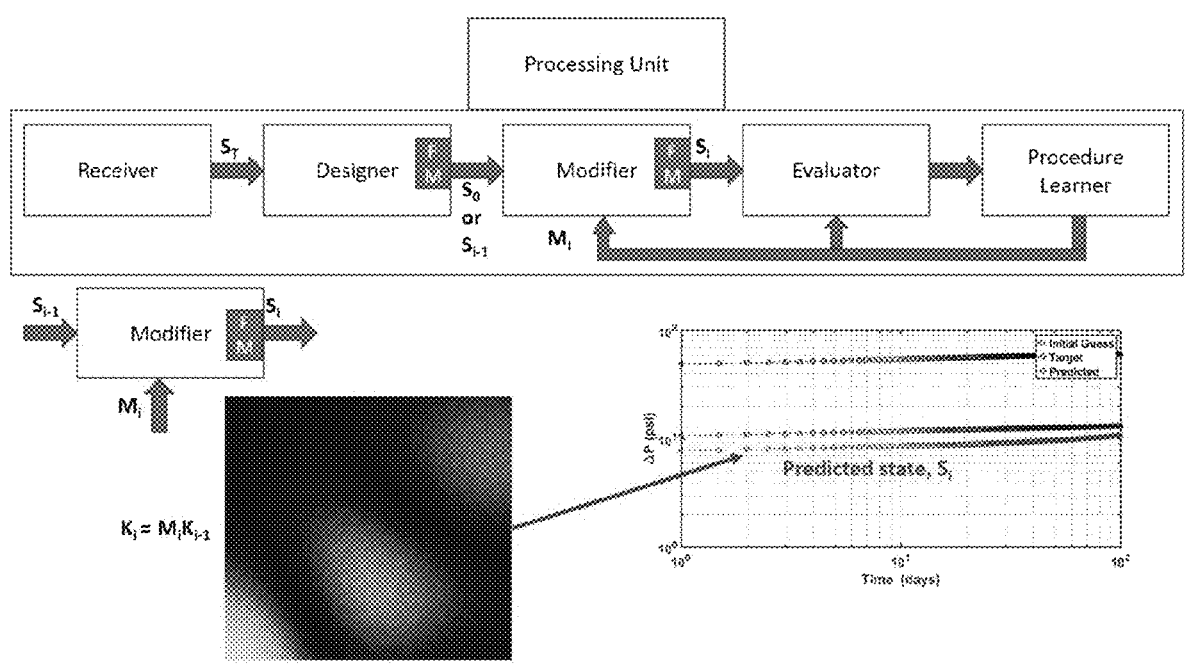
FIG. 15 is a schematic diagram showing that the modifier comprises machine-learning/data-driven algorithms and computational methods to modify the previously built and stored numerical model of the spatial distribution of transport properties in the heterogeneous material at the i-th learning iteration.

FIG. 15 is a schematic diagram 1500 showing that the modifier comprises machine-learning/data-driven algorithms and computational methods to modify the previously built and stored numerical model of the spatial distribution of transport properties in the heterogeneous material at the i-th learning iteration. The modifier does so by applying a modification $M_i$ to old spatial distribution of transport properties $K_{i-1}$ and feeding the new numerical model of the spatial distribution of transport properties in the heterogeneous material to a numerical simulator of wave propagation and/or diffusive transport fronts or full 3D multi-physics simulator for generating simulated temporal measurements related to the transport of energy, mass, and momentum and the temporal measurements related to the gradients that drive the transport processes. Spatial distribution $K_i$ built by the modifier when fed to the simulator/forward-model (denoted by FM) generates a predicted state denoted by $S_i$. Misfit between $S_T$ and $S_i$ guides the learning process.

Figure 16:
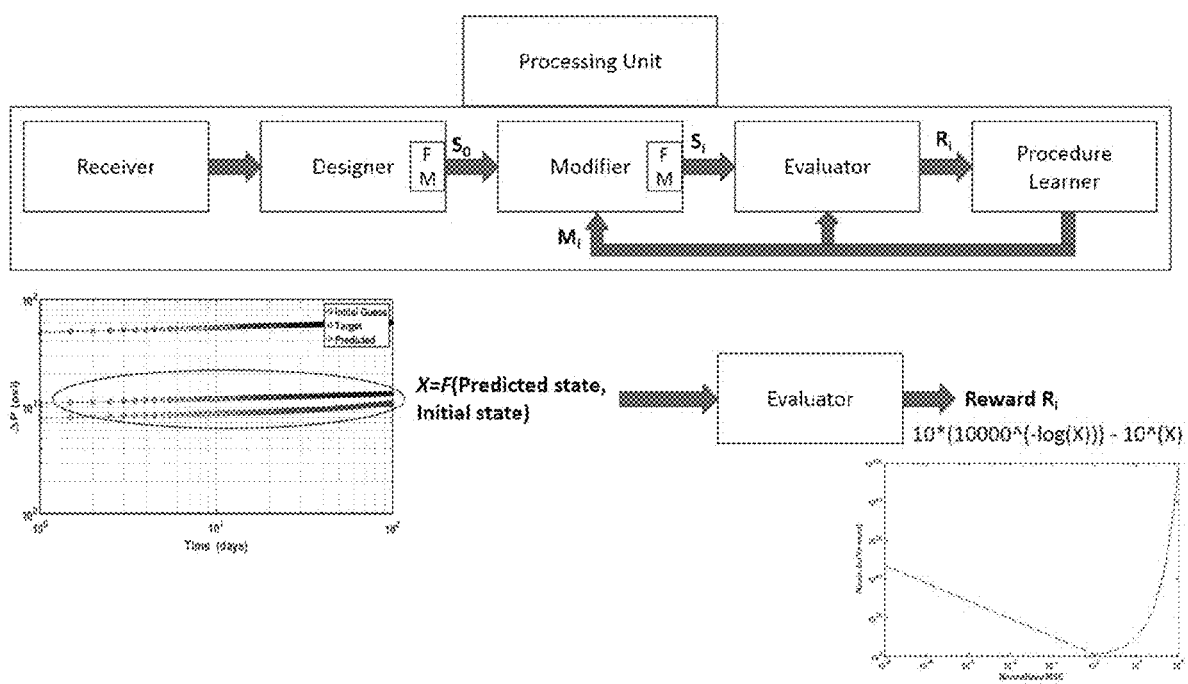
FIG. 16 is a schematic diagram showing that the evaluator comprises machine-learning/data-driven algorithms and computational methods to determine the reward/penalty $R_i$ based on the quality of fit between the simulated $S_i$ and measured $S_T$ temporal measurements.

FIG. 16 is a schematic diagram 1600 showing that the evaluator comprises machine-learning/data-driven algorithms and computational methods to determine the reward/penalty $R_i$ based on the quality of fit between the simulated $S_i$ and measured $S_T$ temporal measurements. The quality of the fit is determined by a function X and the reward is learned based on the temporal measurements and the predictions of the numerical forward model.

Figure 17:
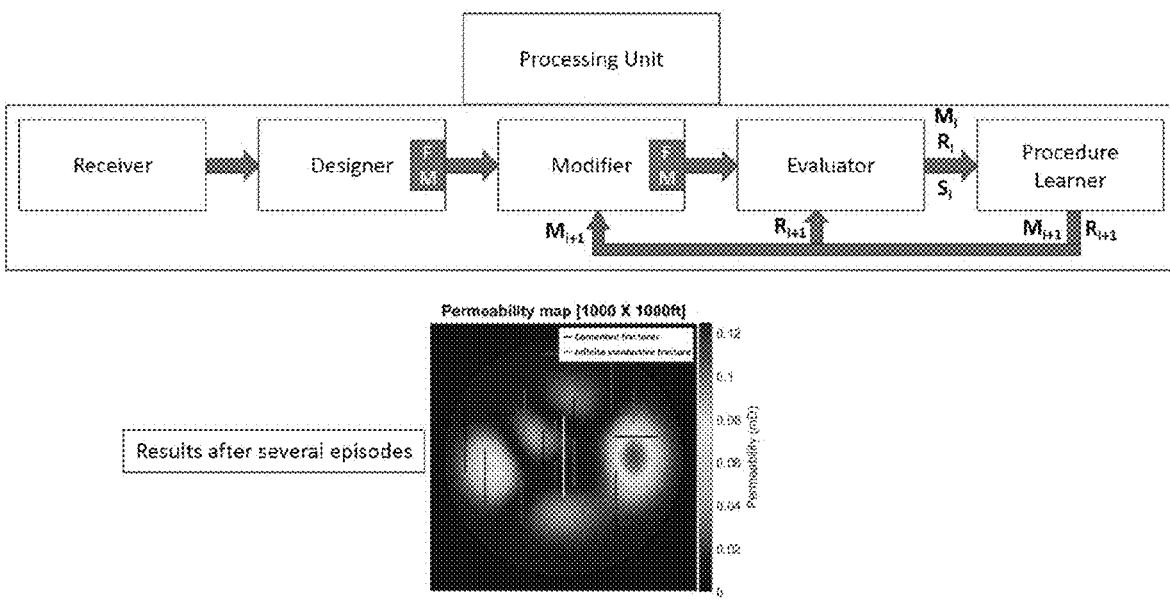
FIG. 17 is a schematic diagram showing that the procedure learner comprises various machine-learning/data-driven algorithms and computational methods to keep track of the modification $M_i$ and the reward $R_i$ for any given misfit observed during the i-th learning iteration.

FIG. 17 is a schematic diagram 1700 showing that the procedure learner comprises various machine-learning/data-driven algorithms and computational methods to keep track of the modification $M_i$ and the reward $R_i$ for any given misfit observed during the i-th learning iteration. The procedure learner does so to learn the best procedure from among the historical experiences comprising modifications $M_i$ rewards $R_i$ and corresponding misfits X that leads to the best fit between the simulated $S_i$ and measured $S_T$ temporal measurements in a limited number of episodes under various scenarios of the spatial distributions of transport properties in the heterogeneous material; to inform the modifier about the modification $M_{i+1}$ of the current transport properties during the next iteration based on the current mismatch; and to inform the evaluator about the best reward $R_{i+1}$ based on the current mismatch and suggested modification $M_{i+1}$. Several learning episodes will lead to a reliable map of spatial distribution of transport properties of the heterogeneous material under the constraints of available data and an available physics-based forward model. In this example, the map indicates spatial distribution of permeability in a heterogeneous ideal cylindrical reservoir. The generation of a reliable map of the spatial distribution of transport properties is referred to as the data-driven intelligent characterization.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A method comprising:
    propagating waves through a well in a sub-surface reservoir comprising a heterogeneous material;
    obtaining, by a receiver in response to the waves, temporal measurements associated with the heterogeneous material, wherein the temporal measurements comprise first temporal measurements associated with transport of energy, mass, or momentum and second temporal measurements associated with gradients resulting from the transport;
    building a numerical model of a material by assigning initial approximations based on the temporal measurements;
    generating simulated temporal measurements using the numerical model;
    determining a reward or a penalty and determining a modification to the numerical model based on a quality of a fit between the temporal measurements and the simulated temporal measurements;
    updating the numerical model based on the modification; and
    iterating the updating based on the reward or the penalty and based on the modification until the quality of the fit is above a threshold.

2. The method of claim 1, wherein the first temporal measurements comprise currents, flow rates, or fluxes.

3. The method of claim 2, wherein the first temporal measurements comprise currents or fluxes.

4. The method of claim 1, wherein the second temporal measurements comprise pressure gradients, voltage gradients, potential gradients, or chemical gradients.

5. The method of claim 4, wherein the second temporal measurements comprise voltage gradients, potential gradients, or chemical gradients.

6. The method of claim 1, wherein the simulated temporal measurements comprise first simulated temporal measurements and second simulated temporal measurements, wherein the first simulated temporal measurements are associated with the first temporal measurements, and wherein the second simulated temporal measurements are associated with the second temporal measurements.

7. The method of claim 1, further comprising further modifying the numerical model using at least one of a machine learning algorithm, a data-driven method, or a computational module.

8. The method of claim 1, further comprising further determining the reward or the penalty and determining the modification using at least one of a machine learning algorithm, a data-driven method, or a computational module.

9. The method of claim 1, further comprising tracking rewards or penalties and tracking modifications for a plurality of iterations.

10. The method of claim 9, further comprising storing experiences based on the tracking.

11. The method of claim 10, further comprising learning policies or procedures based on the experiences.

12. The method of claim 1, wherein the method is independent of user-provided labeling.

13. The method of claim 1, wherein the method is independent of a user-provided training dataset.

14. The method of claim 1, further comprising implementing reinforcement learning (RL).

15. The method of claim 1, wherein the well is a vertical well.

16. The method of claim 1, wherein the sub-surface reservoir is hydrocarbon-bearing.

17. The method of claim 1, further comprising further iterating the updating until the reward is maximized.

18. The method of claim 1, wherein the first temporal measurements are associated with transport of energy, mass, or momentum.

19. A system comprising:
    a first apparatus configured to propagate waves through a well in a sub-surface reservoir comprising a heterogeneous material; and
    a second apparatus coupled to the first apparatus and configured to:
        obtain, in response to the waves, temporal measurements associated with the heterogeneous material, wherein the temporal measurements comprise first temporal measurements associated with transport of energy, mass, or momentum and second temporal measurements associated with gradients resulting from the transport,
        build a numerical model of a material by assigning initial approximations based on the temporal measurements,
        generate simulated temporal measurements using the numerical model,
        determine a reward or a penalty and determine a modification to the numerical model based on a quality of a fit between the temporal measurements and the simulated temporal measurements,
        update the numerical model based on the modification, and
        iterate the updating based on the reward or the penalty and based on the modification until the quality of the fit is above a threshold.

20. The system of claim 19, wherein the first temporal measurements comprise currents, flow rates, or flux.

21. The system of claim 19, wherein the second temporal measurements comprise pressure gradients, voltage gradients, potential gradients, or chemical gradients.

22. The system of claim 19, wherein the simulated temporal measurements comprise first simulated temporal measurements and second simulated temporal measurements, wherein the first simulated temporal measurements are associated with the first temporal measurements, and wherein the second simulated temporal measurements are associated with the second temporal measurements.

23. The system of claim 19, wherein the second apparatus is further configured to further modify the numerical model using at least one of a machine learning algorithm, a data-driven method, or a computational module.

24. The system of claim 19, wherein the second apparatus is further configured to further determine the reward or the penalty and further determine the modification using at least one of a machine learning algorithm, a data-driven method, or a computational module.

25. The system of claim 19, wherein the second apparatus is further configured to:
   track rewards or penalties and track modifications for a plurality of iterations,
   store experiences based on the tracking, and
   learn policies or procedures based on the experiences.

26. A computer program product comprising computer-executable instructions stored on a non-transitory computer-readable medium that, when executed by a processor, cause a system to:
   propagate waves through a well in a sub-surface reservoir comprising a heterogeneous material;
   obtain, in response to the waves, temporal measurements associated with the heterogeneous material, wherein the temporal measurements comprise first temporal measurements associated with transport of energy, mass, or momentum and second temporal measurements associated with gradients resulting from the transport;
   build a numerical model of a material by assigning initial approximations based on the temporal measurements;
   generate simulated temporal measurements using the numerical model;
   determine a reward or a penalty and determine a modification to the numerical model based on a quality of a fit between the temporal measurements and the simulated temporal measurements;
   update the numerical model based on the modification; and
   iterate the updating based on the reward or the penalty and based on the modification until the quality of the fit is above a threshold.

* * * * *